(12) United States Patent
Putz

(10) Patent No.: US 7,255,686 B2
(45) Date of Patent: Aug. 14, 2007

(54) CATHETER ASSEMBLY FOR INTRACRANIAL TREATMENT

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 11/262,367

(22) Filed: Oct. 28, 2005

(65) Prior Publication Data

US 2006/0129102 A1    Jun. 15, 2006

Related U.S. Application Data

(63) Continuation-in-part of application No. 10/423,587, filed on Apr. 25, 2003.

(51) Int. Cl.
*A61M 5/178* (2006.01)

(52) U.S. Cl. .................. 604/164.09; 604/264

(58) Field of Classification Search ........ 604/158–159, 604/241, 164, 165, 264; 606/60, 72, 73; 607/116

See application file for complete search history.

(56) References Cited

U.S. PATENT DOCUMENTS

| | | | |
|---|---|---|---|
| 4,346,709 A | 8/1982 | Schmitt | |
| 4,471,779 A | 9/1984 | Antoshkiw et al. | |
| 4,613,324 A | 9/1986 | Ghajar | |
| 4,685,901 A | 8/1987 | Parks | |
| 4,777,951 A | 10/1988 | Cribier et al. | |
| 4,798,586 A | 1/1989 | Stevens | |
| 4,892,538 A | 1/1990 | Aebischer et al. | |
| 4,903,707 A * | 2/1990 | Knute et al. ............... | 600/561 |
| 4,921,478 A | 5/1990 | Solano et al. | |
| 5,033,998 A | 7/1991 | Corday et al. | |
| 5,041,090 A | 8/1991 | Scheglov et al. | |
| 5,064,654 A | 11/1991 | Berner et al. | |
| 5,081,990 A | 1/1992 | Deletis | |
| 5,087,244 A | 2/1992 | Wolinsky et al. | |
| 5,119,832 A | 6/1992 | Xavier | |
| 5,154,179 A | 10/1992 | Ratner | |
| 5,191,898 A | 3/1993 | Millar | |
| 5,330,768 A | 7/1994 | Park et al. | |
| 5,423,877 A | 6/1995 | Mackey | |
| 5,441,481 A * | 8/1995 | Mishra et al. ............... | 604/29 |
| 5,458,631 A | 10/1995 | Xavier | |
| 5,505,698 A | 4/1996 | Booth et al. | |

(Continued)

*Primary Examiner*—Nicholas Lucchesi
*Assistant Examiner*—Theodore J. Stigell
(74) *Attorney, Agent, or Firm*—Jansson Shupe & Munger Ltd.

(57) ABSTRACT

A catheter assembly for intracranial treatment of a patient is provided having both outer and inner catheters. The outer catheter has at least one element and defines a lumen in communication with at least one aperture and an opening. The inner catheter is sized to be received within the lumen and includes a passageway in communication with at least one port. The element can be in the form of a contact or sensor. The outer catheter can include an inflatable balloon distal to an element. The balloon is adapted to seal upon inflation the tract created by the outer catheter when inserted into the brain. The outer catheter may have a flexible channel extending outward from the body of the catheter that permits the inner catheter to be inserted into the body through the channel. The inner catheter is preferably configured for removable engagement to a tapered fitting on the outer catheter.

24 Claims, 8 Drawing Sheets

U.S. PATENT DOCUMENTS

| | | |
|---|---|---|
| 5,662,607 A | 9/1997 | Booth et al. |
| 5,676,655 A | 10/1997 | Howard et al. |
| 5,697,975 A | 12/1997 | Howard et al. |
| 5,711,316 A | 1/1998 | Elsberry et al. |
| 5,713,858 A | 2/1998 | Heruth et al. |
| 5,728,066 A | 3/1998 | Daneshvar |
| 5,782,798 A | 7/1998 | Rise |
| 5,792,100 A | 8/1998 | Shantha |
| 5,792,110 A | 8/1998 | Cunningham |
| 5,795,331 A | 8/1998 | Cragg et al. |
| 5,807,328 A | 9/1998 | Briscoe |
| 5,810,767 A | 9/1998 | Klein |
| 5,843,022 A * | 12/1998 | Willard et al. ............ 604/30 |
| 5,868,704 A | 2/1999 | Campbell et al. |
| 5,975,085 A | 11/1999 | Rise |
| 6,017,323 A | 1/2000 | Chee |
| 6,041,252 A | 3/2000 | Walker et al. |
| 6,096,021 A | 8/2000 | Helm et al. |
| 6,120,477 A | 9/2000 | Campbell et al. |
| 6,203,526 B1 * | 3/2001 | McBeth et al. .......... 604/96.01 |
| 6,210,346 B1 | 4/2001 | Hall et al. |
| 6,251,115 B1 | 6/2001 | Williams et al. |
| 6,263,225 B1 | 7/2001 | Howard, III |
| 6,264,633 B1 | 7/2001 | Knorig |
| 6,272,370 B1 * | 8/2001 | Gillies et al. ............... 600/411 |
| 6,283,951 B1 | 9/2001 | Flaherty et al. |
| 6,510,347 B2 | 1/2003 | Borkan |
| 6,527,782 B2 | 3/2003 | Hogg et al. |
| 6,629,990 B2 | 10/2003 | Putz et al. |
| 6,656,152 B2 | 12/2003 | Putz |
| 6,733,474 B2 | 5/2004 | Kusleika |
| 6,773,447 B2 | 8/2004 | Laguna |
| 6,832,115 B2 | 12/2004 | Borkan |
| 6,887,229 B1 | 5/2005 | Kurth |

* cited by examiner

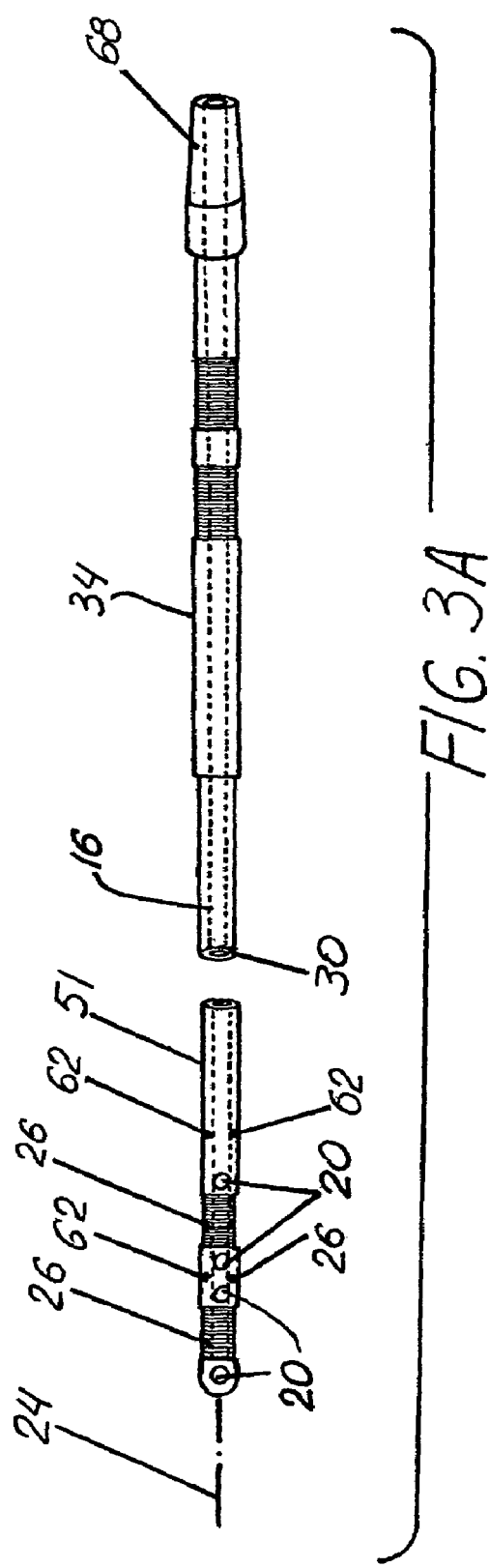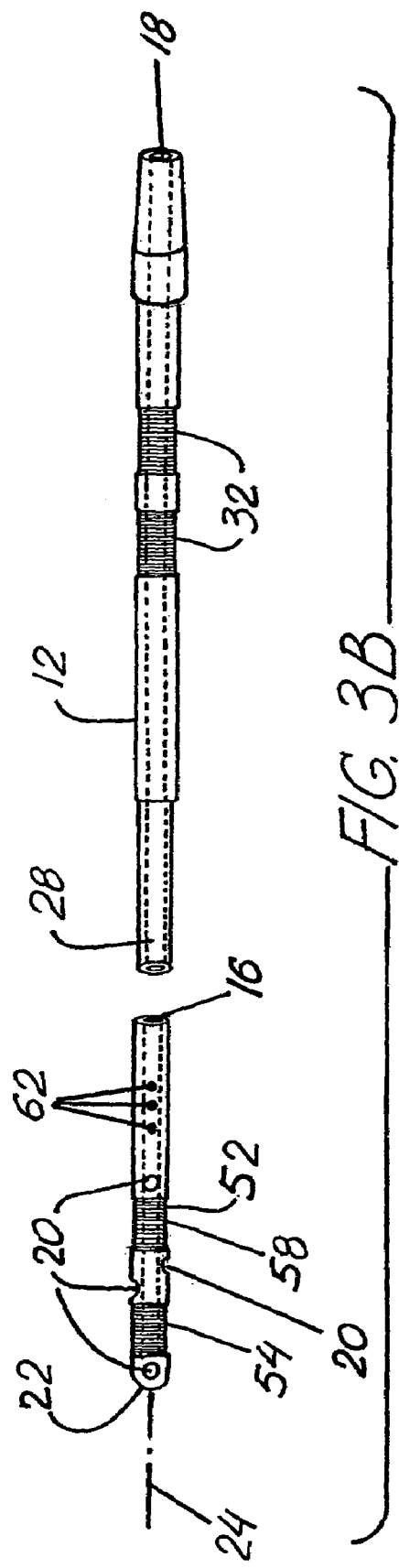

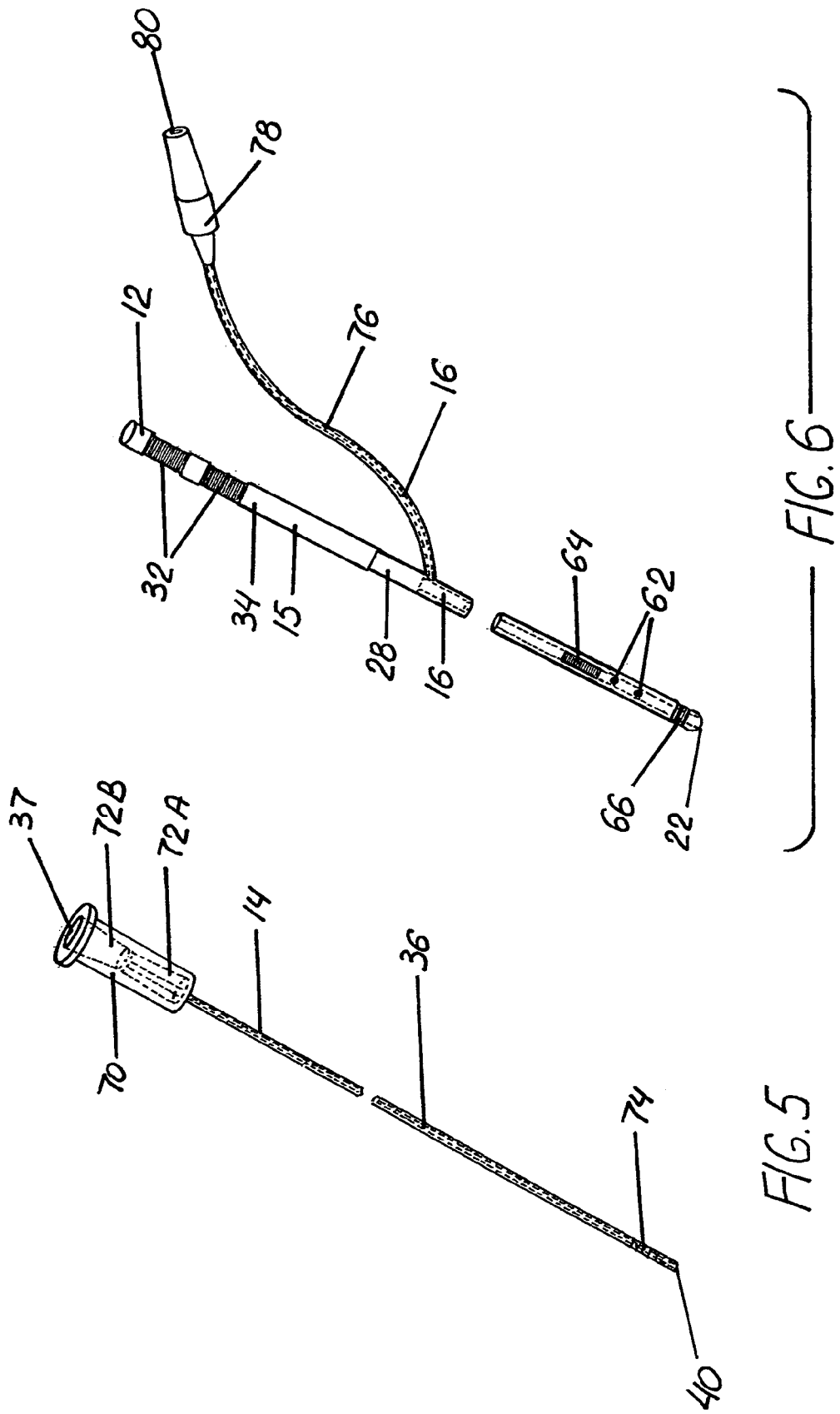

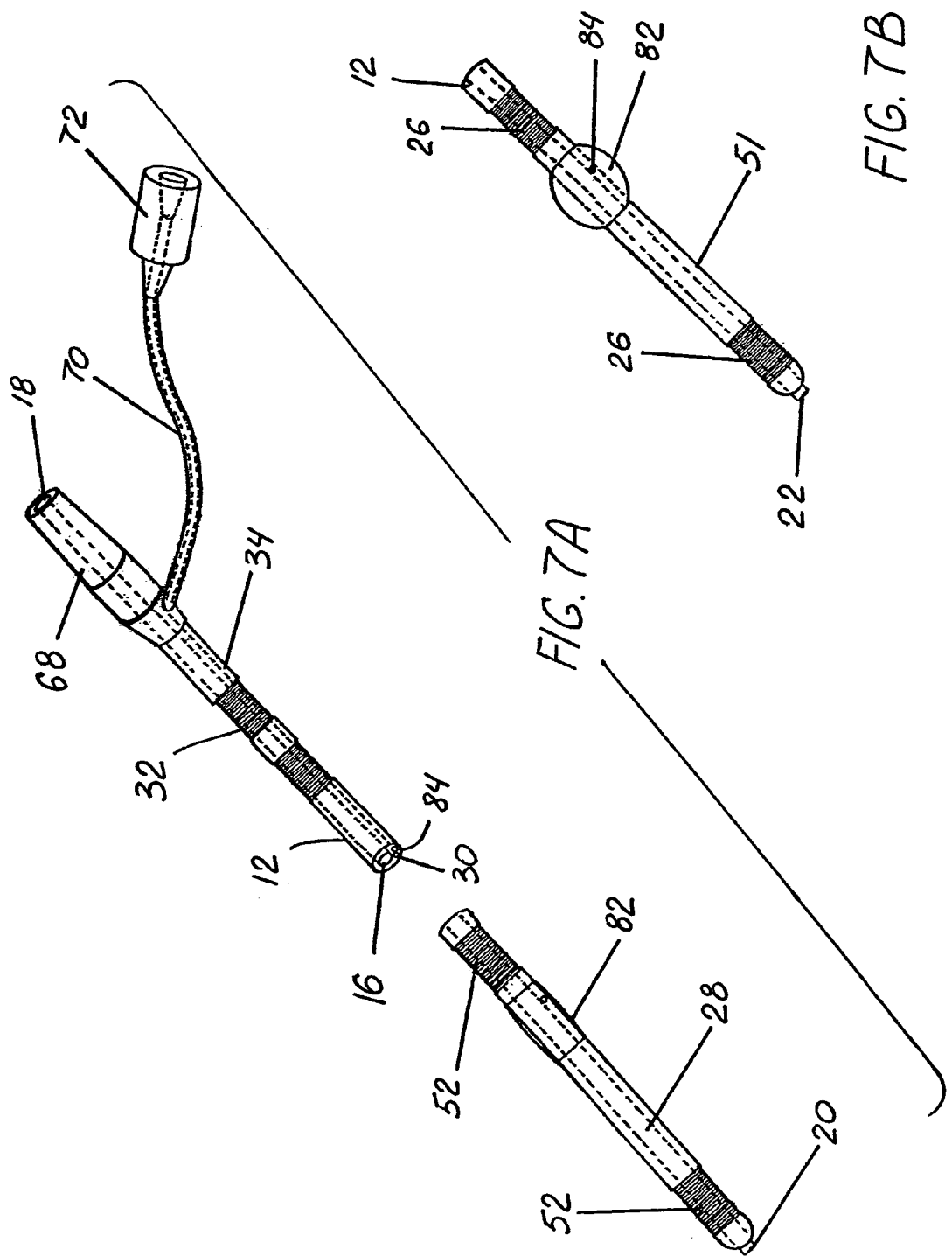

CATHETER ASSEMBLY FOR INTRACRANIAL TREATMENT

RELATED APPLICATION

This application is a continuation-in-part of U.S. patent application Ser. No. 10/423,587, filed on Apr. 25, 2003, now allowed.

FIELD OF INVENTION

The present invention relates to catheter assemblies for intracranial treatment and, in particular, to catheter assemblies for the intracranial transfer of fluids.

BACKGROUND OF THE INVENTION

Movement disorders such as epilepsy and Parkinson's disease have been estimated to affect some 1–2% of the developed world's population and up to 10% of people in underdeveloped countries. Currently, approximately 75% of those who suffer from movement disorders are responsive in some degree to drugs.

Electrical stimulation has also been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

In treatment, electrical stimulation has been used with the recording and analysis of changes in brain activity to predict the occurrence of epileptic seizures. The time of onset of such seizures is often predictable by neural discharge monitoring, even when the exact causal nature of precipitating dysfunction is not understood. Electrodes have been used to obtain signals representative of current brain activity along with a signal processor for continuous monitoring and analysis of these electrical signals in order to identify important changes or the appearance of precursors predictive of an impending change.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

Improved intracranial monitoring devices have been shown to facilitate treatments of movement disorders. Monitoring is typically performed by instruments which are inserted into the brain at different locations or along different tracks. Other systems employ a single device which must be removed and reinserted to provide for delivery of multiple drugs or use of different electrical devices.

Since the introduction of probes or other similar devices into the brain is common in many surgical procedures today, there are a variety of probes available. Such probes typically include ports for drug delivery or electrical, chemical, electrochemical, temperature and/or pressure contacts which enable the observation and analysis of the brain state or contacts providing stimulation. These ports and contacts must typically be positioned at specific points or regions in the brain.

Probes used in intracranial penetration are typically fabricated so that their introduction to the brain is as minimally traumatic as possible. In addition to being minimally traumatic during insertion, certain inserted probes must also be able to remain implanted without causing injury through unintended movement. In some uses, a probe may be implanted and remain in the patient's brain for weeks or longer. Changes in the positioning of the probe often occur during placement or during such extended periods. Therefore, the probe must be capable of precise placement and as bio-compatible as possible. In response to these requirements, state of the art intracranial probes are typically thin, flexible pieces with smooth surfaces to minimize the amount of brain tissue contacted and to minimize damage to contacted brain tissue.

While such thin, flexible probes are sufficiently biocompatible, they are delicate and often difficult to insert along specific trajectories or lines of insertion. During typical implantation, a surgeon feeds the probe into the brain through an aperture in the skull. In this process, the surgeon has very little control over the distal end of the probe. In order to provide more rigidity to the probe to overcome this problem, a removable stylet may be inserted into the probe before implantation. Still, veering from the intended line of insertion is not altogether prevented by introduction of a stylet to the probe.

There is a continuing significant need in the field of intracranial treatment, particularly with insertion of probes into the interior of the brain, for improvements in accuracy of insertion and avoidance of injury, while retaining efficiency and ease of use.

In addition, there is a need in the field of intracranial treatment to minimize the invasiveness of intracranial treatment and to reduce the number of instruments which penetrate brain tissue or the number of times a single instrument must penetrate brain tissue.

Furthermore, there is a need in the field of intracranial treatment to provide the ability to precisely locate the position of a probe during insertion to ensure proper positioning.

OBJECTS OF THE INVENTION

It is a primary object of the invention to provide an improved intracranial catheter assembly that overcomes some of the problems and shortcomings of the prior art.

Another object of the invention is to provide a novel catheter assembly which is simple in structure and operation in order to facilitate intracranial procedures.

Another object of the invention is to provide an exceptional catheter assembly having an outer catheter with a body adapted to avoid extensive trauma to and scarring of brain tissue and inserted into a targeted area of the brain is used to reliably guide an inner catheter to a specific tissue region for the precise delivery of a fluid in the form of a drug.

Another object of the invention is to provide an excellent catheter assembly having an outer catheter that includes contacts for stimulation and/or for monitoring the brain and that receives and guides an inner catheter for delivering a drug to targeted brain tissue.

Another object of the invention is to provide a desirable catheter assembly having an outer catheter provided with an inflatable balloon capable of sealing off the insertion tract formed by the catheter to prevent a drug being introduced into the brain by the assembly from migrating back through the tract and further allows for the monitoring of cellular function within the brain prior to and after introduction of the drug.

Another object of the invention is to provide a novel catheter assembly having an outer catheter that includes a permeable balloon capable of being inflated with a drug for introduction of the drug into the brain at a controlled rate.

Yet another object of the invention is to provide an improved catheter assembly having an outer catheter that includes elements for sensing and/or monitoring brain activity and that receives and guides a micro-dialysis catheter to a selected area of the brain for sampling cerebral spinal fluid through a dialysis membrane.

SUMMARY OF THE INVENTION

The invention is for a catheter assembly to provide intracranial treatment of a patient. The catheter assembly comprises both outer and inner catheters. The outer catheter has at least one element and defines a lumen in communication with at least one aperture and an opening. The inner catheter is sized to be received within the lumen and includes a passageway in communication with at least one port. Highly desirable is where the port includes a dialysis membrane adapted to receive cerebral spinal fluid.

In certain preferred embodiments, the catheter assembly also includes a rigid stylet that is sized to be received within the lumen. The stylet aids in the insertion of the outer catheter into the brain and is removed prior to the insertion into the lumen of the inner catheter. Also desirable is where the aperture on the outer catheter is in axial alignment with the lumen.

One much preferred embodiment finds the outer catheter having a closed distal end and the aperture is spaced from the distal end along the distal portion of the catheter. Most desirable is where the outer catheter has first and second apertures in communication with the lumen and these apertures are spaced axially along its distal portion. Highly preferred is where the first and second apertures are spaced radially about the axis of the catheter also along its distal portion.

In another desirable embodiment, the inner catheter has at least two ports communicating with the passageway where these ports are spaced axially along the catheter's distal portion. Also preferred is where the inner catheter has two ports that are spaced radially about the axis of the catheter as well as spaced axially along its distal portion.

Certain appreciated examples of this invention have a contact that monitors brain activity as the element. Much appreciated is where this contact is monitoring electrical activity within the brain. Also preferred is where the contact is a micro-contact.

A location marker to identify the position of the outer catheter when it is inserted within the brain serves as the element in a number of interesting cases of this catheter assembly. Also interesting is where the element is at least one sensor, preferably a sensor that can sense temperature changes within the patient's brain. Highly preferred is where the element is a contact providing electrical stimulation to a tissue region within the brain.

Many desirable embodiments of this invention provide the outer catheter with a plurality of elements spaced axially and radially along its distal portion. Other preferred embodiments provide the outer catheter with a proximal-contact along its proximal portion where the proximal-contact is conductively connected with at least one element through a lead. Much preferred in such embodiments is where the lead is electrical wiring. Also highly desirable is where the lead is a fiber-optic bundle.

Most preferred is where the outer catheter comprises a body that includes the proximal portion with its proximal-contact and the lumen includes a flexible channel that extends outward from the body at a point distal to the proximal-contact such that the channel defines the opening of the outer catheter. This channel communicates with the portion of the lumen within the body and allows the inner catheter to be inserted into the body through the channel opening.

Certain desirable cases of this invention find the outer catheter having a proximal end where the opening is positioned. With such embodiments, more desirable is where the outer catheter includes a tapered fitting at its proximal end that is configured for removable engagement to a fitting at the proximal end of the inner catheter.

An interesting and preferred catheter assembly has a conduit extending from the proximal portion of the outer catheter to an inflatable balloon secured to its distal portion. Most desirable is where the balloon is inflatable with at least one drug and the balloon is formed from a material permeable to this drug so that the drug can be introduced into the brain through the balloon. Also preferred is where the balloon is adapted to seal upon inflation the intracranial tract created by the outer catheter when it is inserted into the brain. A very appreciated embodiment has the balloon positioned along the outer catheter's distal portion at a point proximal to the aperture and distal to the element.

In many desired embodiments, the outer catheter of the assembly is adapted to be secured to the patient's skull following placement of the catheter in the targeted region. Much preferred is where the proximal portion of the outer catheter is externally-threaded so that it can be screwed into the skull. Highly desirable in these embodiments is where the inner catheter fittingly engages the outer catheter, preferably by providing the inner catheter with a externally-threaded proximal portion threadably received by the outer catheter, to firmly secure the one to the other. Most desirable is where the inner catheter also includes a flexible conduit that extends outward from the proximal fitting to a tapered inlet. The inlet communicates with the inner catheter's passageway in a manner that allows a pumping instrument to be connected to the inlet so that a fluid can be transferred through the passageway.

BRIEF DESCRIPTION OF THE DRAWINGS

FIGS. 3A and 3B are perspective views of alternate preferred outer catheters in accordance with this invention with cut-away sections to reveal and dashed lines to represent otherwise unseen internal features.

FIG. 5 is a perspective view of an inner catheter having a micro-dialysis membrane in accordance with this invention with a cut-away section and dashed lines to represent otherwise unseen internal features.

FIG. 6 is a perspective view of an alternate outer catheter having a flexible channel extending outward from the body in accordance with this invention with a cut-away section to reveal and dashed lines to represent otherwise unseen internal features.

FIG. 7A is a perspective view of a preferred outer catheter having a balloon shown deflated in accordance with this invention with cut-away sections to reveal and dashed lines to represent otherwise unseen internal features.

FIG. 7B is the distal end of the outer catheter of FIG. 7A showing the balloon inflated with cut-away sections to reveal and dashed lines to represent otherwise unseen internal features.

DETAILED DESCRIPTION OF PREFERRED EMBODIMENTS

Figure 1:
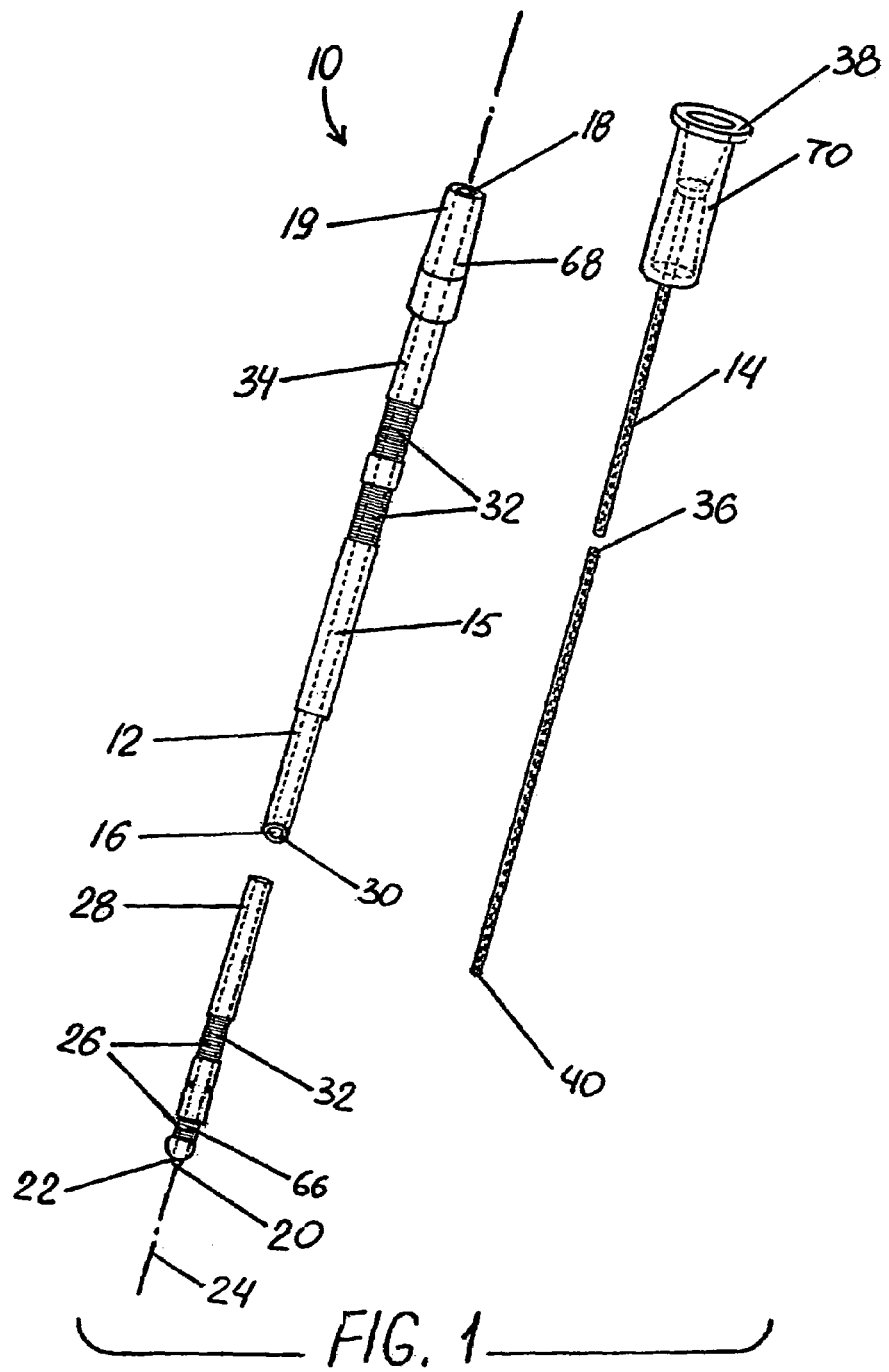
FIG. 1 is a perspective view of a preferred catheter assembly in accordance with this invention with cut-away sections to reveal and dashed lines to represent otherwise unseen internal features.

The figures illustrate preferred embodiments of an improved catheter assembly for intracranial treatment of a patient in accordance with this invention. FIG. 1 is a perspective view of catheter assembly 10 comprising of an outer catheter 12 and an inner catheter 14. Outer catheter 12 and inner catheter 14 cooperate to transfer a fluid, preferably a drug, to a targeted area of a patient's brain.

Outer catheter 12 is an elongated, tubular structure having a diameter preferably between about 0.6 and 3.0 millimeters, most preferably about 1.0 millimeter. As illustrated in FIG. 1, outer catheter 12 is provided with a body 15 that defines a lumen 16. Lumen 16 extends from opening 18 at proximal end 19 and is in communication with aperture 20. Body 15 is open at distal end 22 to form aperture 20. Opening 18 and aperture 20 are coaxial with lumen 16 along central axis 24 of body 15.

Lumen 16 is a tubular channel extending for some length within outer catheter 12 and sized to receive inner catheter 14, i.e., having a diameter slightly greater than the outside diameter of inner catheter 14. Lumen 16 preferably has a diameter of 0.5 millimeters or less.

Outer catheter 12 further includes elements 26 secured to the distal portion 28 of body 15 above distal end 22. Elements 26 are conductively connected by leads 30 (seen in FIG. 1 running alongside lumen 16) to proximal-contacts 32. Leads 30 can be in the form of electrical wiring or a fiber-optic bundle. Proximal-contacts 32 are mounted along the proximal portion 34 of body 15. When outer catheter 12 is inserted into the brain, proximal-contacts 32 remain outside of the patient. Proximal-contacts 32 are preferably formed from stainless steel or similar alloys or materials that are non-corrosive conductors and that can endure sterilization.

Outer catheter 12 is preferably substantially flexible, formed from bio-compatible materials such as polyurethane, silicone, or polyimide. In certain embodiments, outer catheter 12 can also be in the form of a cannula made from a substantially rigid material that is preferably MRI safe/compatible. Such preferable materials are platinum, titanium, polyimide-coated glass, and other non-ferrous alloys. During surgery, when in the form of a cannula, outer catheter 12 could be used with a stereotatic frame or a frameless guidance system to accurately position the catheter within the brain.

Inner catheter 14 is preferably made from flexible, bio-compatible materials such as silicone, polyimide, or polyimide-coated glass. Inner catheter 14 is provided with passageway 36 which extends from mouth 37 at proximal end 38 to port 40. As depicted in FIG. 1, port 40 is coaxial with passageway 36. Applicant notes that one such preferred catheter is disclosed in U.S. patent application Ser. No. 10/423,587 filed by Applicant on Apr. 25, 2003, the disclosure of which is incorporated by reference herein.

Figure 2:
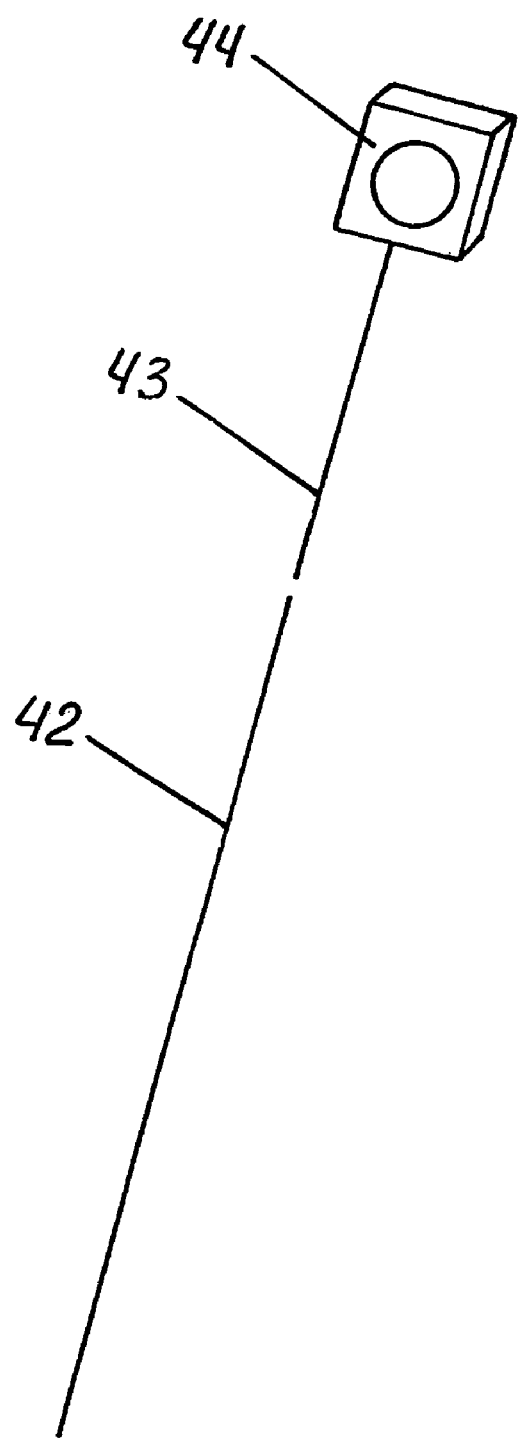
FIG. 2 is a perspective view of a preferred stylet in accordance with this invention with a cut-away section.

Catheter assembly 10 preferably also includes stylet 42 which is shown in FIG. 2. Stylet 42 has a shaft 43 and an enlarged handle 44 at the proximal end. Shaft 43 has a diameter or thickness slightly smaller than the diameter of lumen 16 so that stylet 42 is receivable within lumen 16 for use during insertion of outer catheter 12 into the brain. Stylet 42 is rigid to allow for precise positioning of outer catheter 12 inside the brain. Stylet 42 is preferably formed from stainless steel, tungsten or other non-ferrous MRI safe/compatible alloys. Stylet 42, in addition to providing rigidity to outer catheter 12 for its precise positioning within the brain, prevents brain tissue from entering lumen 16 through aperture 20 during insertion. Following insertion of outer catheter 12 into the brain, stylet 42 is removed to allow inner catheter 14 to be received within lumen 16.

As seen in FIGS. 3A and 3B, other preferred embodiments of outer catheter 12 have a closed distal end 22 and a plurality of apertures 20, each aperture 20 in communication with lumen 16. Apertures 20 in FIG. 3A are positioned above distal end 22 and spaced in axial alignment with axis 24 along distal portion 28. Apertures 20 in FIG. 3B are shown axially and radially spaced about axis 24. One skilled in the art will recognize that these configurations can also include an aperture 20 forming an open distal end 22 as depicted in FIG. 1.

Figure 4A:
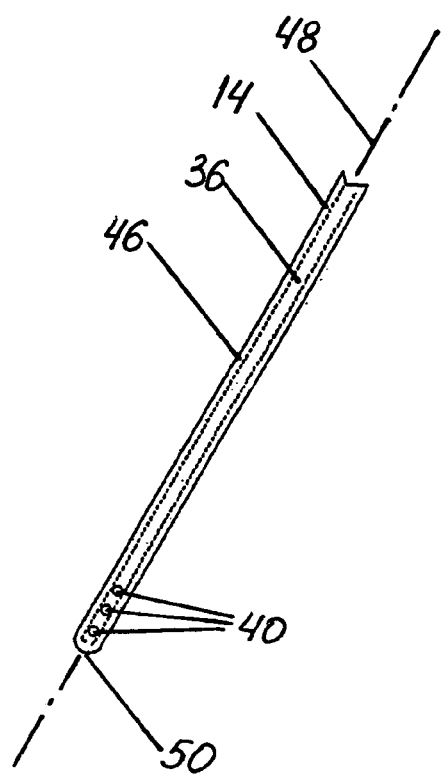
FIGS. 4A and 4B are perspective views of the distal portions of alternate preferred inner catheters in accordance with this invention with dashed lines to represent otherwise unseen internal features.
Figure 4B:
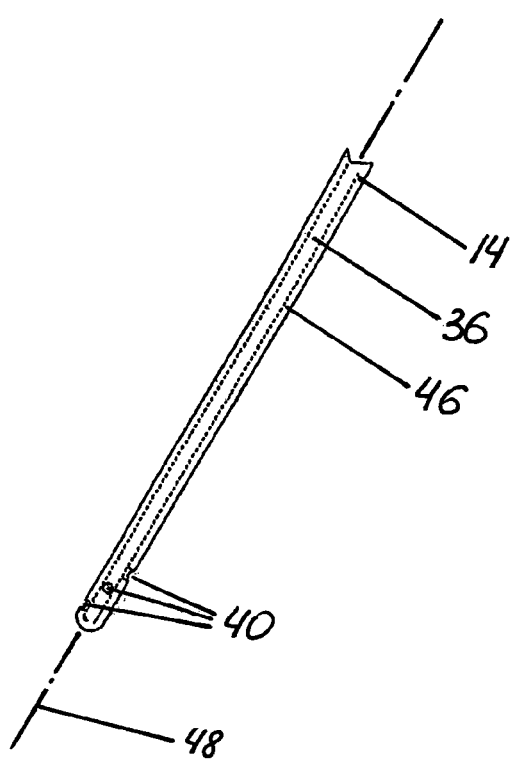

The distal portion 46 of alternate embodiments of inner catheter 14 are illustrated in FIGS. 4A and 4B. Each has a plurality of ports 40 in fluid communication with passageway 36. One arrangement of ports is depicted in FIG. 4A where each port 40 is spaced along distal portion 46 in axial alignment with central axis 48 of inner catheter 14. Another arrangement is seen in FIG. 4B where each port 40 is axially and radially spaced about distal portion 46. It should be understood that inner catheter 14 can have a port 40 coaxial with passageway 36 such as to form an open distal end 50

(as seen in FIG. 1) as well as or in addition to ports 40 positioned along the distal portion 46 adjacent to the distal end 50.

Elements 26 provide for monitoring of brain activity, for stimulating brain tissue or for serving as a location beacon to aid in determining the precise position of distal portion 20 within the brain. Elements 26 are preferably positioned on the exterior 51 of distal portion 28. Elements 26 can take the form of contacts 52, as illustrated in FIGS. 1, 3A, and 3B. Contacts 52 comprise devices such as electrodes 54 designed to monitor brain activity in a desired tissue region of the brain 56 through the sensing of electrical and/or electrochemical changes within the brain as well as electrodes 58 designed to provide electrical stimulation to specific areas of the brain. Electrodes serving as contacts 52 are preferably constructed from platinum, platinum-iridium or other bio-compatible conductive material. Electrodes can be macro-contacts 60 that circumscribe or band body 15 or micro-contacts 62 capable of measuring electrical changes at the level of a single neuron.

Elements 26 can also can take the form of a sensor 64 as depicted in FIG. 5. Sensors 64 are designed to monitor brain activity within select tissue regions through the sensing of electrical, electrochemical, chemical, temperature or pressure changes within the brain. Sensors 64 can be electrochemical and optical transducers designed to measure chemical, pressure, temperature, cerebral blood flow and other physiological changes in the brain. Such devices are known in the art and are preferably less than about 2 millimeters long. Sensor 64 is preferably in the form of a temperature sensor.

Elements 26 may further be in the form of a location marker 66 as seen in FIGS. 1 and 5. Location marker 66 is preferably a structure comprised of a non-ferrous material known in the art such as gold or tungsten that has an image signal intensity suitable for proton magnetic resonance imaging (MRI) with most commercial machines and is also sufficiently x-ray opaque for satisfactory imaging using computed tomographic scanning (CT) or on X-ray. Location marker 66 can also be comprised of a sensor capable of measuring voltages induced by a transmitted magnetic field that can be used to identify the position and orientation of the sensor within that field.

Elements 26 may be positioned on both the distal and proximal sides of apertures 20 along distal portion 22 as seen in FIGS. 3A and 3B. This configuration allows for monitoring of cellular function within the tissue region of the brain 56 being targeted prior to treatment to verify the presence of diseased brain cells. Upon verification of diseased tissue within the targeted region, delivery of a drug or other treatment agent can commence through catheter assembly 10 while monitoring of the tissue region 56 continues concurrently with such treatment. This can have particular value in the treatment of different tissue regions of the brain for movement disorders such as Parkinson's Disease.

FIGS. 3A and 3B show that macro-contacts 60 are spaced axially along distal portion 28. Micro-contacts 62 can be spaced axially along distal portion 28 as illustrated in FIG. 3B or spaced radially around body 15 as shown in FIGS. 1 and 3A.

Proximal end 19 of outer catheter 12 is provided with a tapered fitting 68, preferably a male luer conical fitting, abutting opening 18. Proximal end 38 of inner catheter 14 is provided with a tapered coupler 70, preferably a luer coupler that has female luer fittings 72A, 72B at both of its ends. Tapered coupler 70, as illustrated in FIG. 6A, enables inner catheter 14 to form a detachable fluid-tight coupling with outer catheter 12 when inner catheter 14 is fully inserted into lumen 16 through opening 18. Tapered fitting 68 of outer catheter 12 is snugly received by fitting 72A at the distal end of tapered coupler 70 on inner catheter 14. Fitting 72B on the proximal end of tapered coupler 70 enables inner catheter 14 to be operatively connected by tubing to an external piece of equipment such as a pump. One skilled in the art will recognize that inner catheter 14 could also be connected to internal instrumentation having pumping capability. This process enables treatments agents such as drugs to be administered to a specific tissue region of the brain 56 through inner catheter 14 via port 40 either directly as when inner catheter 14 has been extended through aperture 20 as shown in FIG. 6A or indirectly by way of aperture 20 as when distal end 50 of inner catheter 14 remains within outer catheter 12.

FIG. 5 depicts an inner catheter 14 having a dialysis membrane, preferably provided with a micro-dialysis membrane 74, adjacent to port 40. After positioning outer catheter 12 in a targeted region of the brain, inner catheter 14 is inserted along lumen 16 so that apertures 20 of outer catheter 12 allow cerebral spinal fluid (CSF) to reach membrane 74. CSF moves through membrane 74 and is transferred through passageway 36 to external receptacles or analysis devices via pumping equipment.

In FIG. 6, an outer catheter 12 is shown having a lumen 16 that branches off from body 15 distal to proximal-contacts 32 and extends outward through flexible channel 76, terminating at a tapered fitting 78 (similar in type to fitting 68) with channel opening 80. Inner catheter 14 is received by lumen 16 through opening 80 and travels into body 15 towards distal end 22 of outer catheter 12. Inner catheter 14 is preferably sufficiently flexible to navigate lumen 16.

FIG. 7A illustrates a catheter assembly 10 with inner catheter 14 fully inserted within outer catheter 12. Outer catheter 12 is shown in FIGS. 7A and 7B having an inflatable balloon 82 rigidly mounted to distal portion 28, preferably above aperture 20 and both proximal from and distal to elements 26. As seen in FIG. 7A, a conduit 84 enters body 15 along proximal portion 34 and runs alongside lumen 16, terminating at balloon 82. Conduit 84 is preferably tubing made of polyurethane. Conduit 84 provides for the introduction of a fluid to inflate balloon 82 and, if necessary to withdraw fluid from balloon 82 to cause deflation. Conduit 84 originates at injection port 86 that can be operatively connected to an external device such as a pump to dispense or receive the fluid.

Following placement of distal portion 28 of outer catheter 12 within the brain, balloon 82 can be inflated to block or occlude the insertion tract 88 created during the insertion process. This inhibits any drug administered to a tissue region of the brain 56 through aperture 20 from migrating back through the tract. Balloon 82 is preferably made from an elastomeric material so that it can achieve complete deflation when outer catheter 12 is later withdrawn from the brain.

In certain embodiments, balloon 82 is permeable. Balloon 82 in these embodiments can be inflated with a drug or other fluid intended to be administered to the brain whereby the drug then permeates through the wall of balloon 82 to treat the tissue region of the brain 56 surrounding balloon 82. In this manner, a drug can be introduced to one targeted tissue region of the brain delivered by outer catheter 12 through aperture 20 at the same time the same or a different drug is transferred to another selected tissue region through permeable balloon 82. Balloon 82 is preferably adapted to administering a drug to the brain slowly over a period of time, thereby allowing for the effective introduction of the drug to the desired tissue region. This is especially desirable where there is a void in the particular tissue region due to some structure such as a tumor being removed. Inflating balloon 82 within the void permits the medication to be more effectively transferred to all of the affected tissue that surrounds the outside of the balloon.

One skilled in the art will recognize that balloon 82 can be made permeable by forming balloon 82 from a naturally porous material such as polytetrafluroethylene (PTFE) or from an elastomeric material having perforations formed in the wall of the balloon. The balloon wall is preferably from 0.5 to 5.0 mils in thickness. Where the balloon wall is perforated, an array of minute perforations, each having a diameter of 5 to 30 microns, is preferably uniformly spaced apart and concentrated along a central band circumscribing balloon 82. Concentration of the perforations within such a region in the middle of balloon 82 provides for focused delivery of the drug by limiting the area of permeation to just the surface area of balloon 82 making conforming contact with the surrounding brain tissue.

Figure 8:
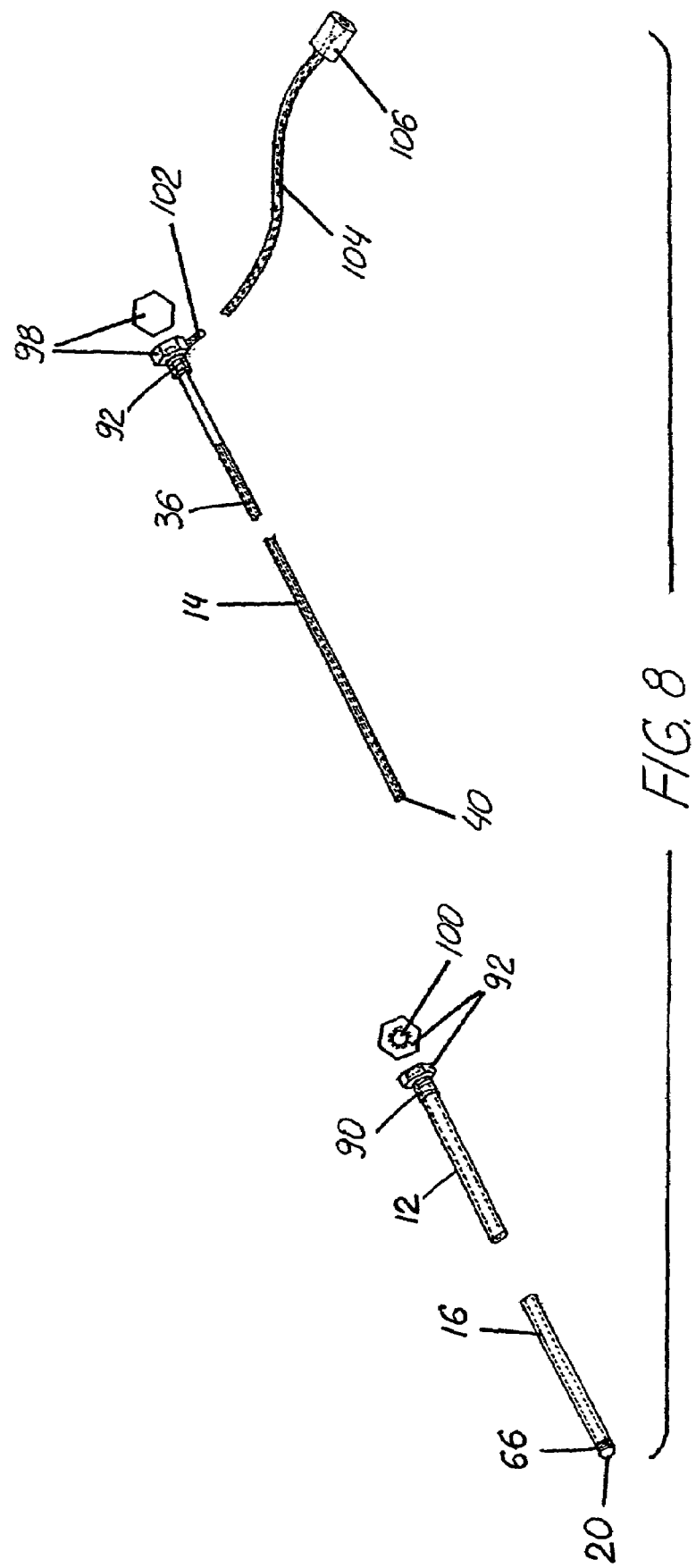
FIG. 8 is a perspective view of another preferred outer catheter and inner catheter in accordance with this invention with cut-away sections and dashed lines representing otherwise unseen internal features along with top views of the heads of both catheters.
Figure 9:
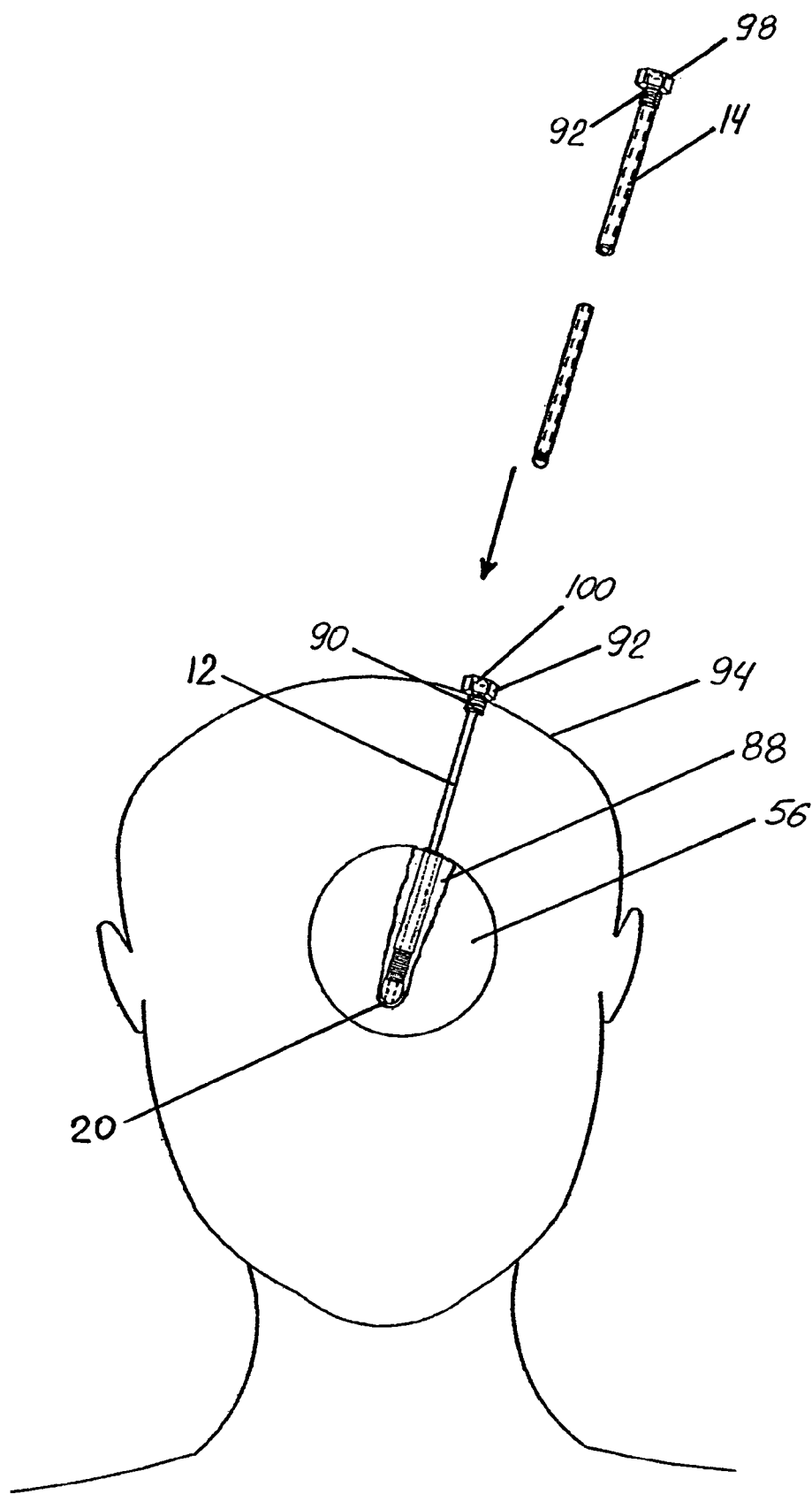
FIG. 9 is a schematic view illustrating the outer catheter of FIG. 8 positioned within the brain and prepared to receive the inner catheter of FIG. 8.

As seen in FIGS. 8 and 9, outer catheter 12 can further include a threaded exterior portion 90. Threaded portion 90 preferably abuts a hexagonal head 92 at the proximal end 19 of outer catheter 12. Outer catheter 12 can be firmly secured to the patient by screwing threaded portion 90 into the skull 94 using the head 92 of the catheter.

Each inner catheter 14 comprising catheter assembly 10 with this embodiment of outer catheter 12 also includes a threaded proximal portion 96 immediately beneath the head 98 of inner catheter 14. Head 92 of outer catheter 12 is provided with a threaded opening 100 coaxial with lumen 16. Upon inserting inner catheter 14 through opening 100 into lumen 16, inner catheter 14 is firmly secured to outer catheter 12 by screwing threaded portion 96 into threaded opening 100 utilizing head 98.

Outer catheter 12 in this manner serves as a trajectory catheter. Outer catheter 12 preferably includes location marker 66 to aid in positioning outer catheter 12 at the desired location in a targeted tissue region of the brain 56. Head 98 of inner catheter 14 is preferably provided with a fitting 102 in communication with passageway 36 to which a flexible conduit 104 such as polyurethane tubing can be attached. Conduit 104 extends outward and terminates at a tapered inlet 106. Tapered inlet 106 is preferably a luer fitting to which an external apparatus such as a pump can be connected to permit a liquid treatment agent or other fluid to be injected into and/or withdrawn from tissue region 56.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A catheter assembly for intracranial treatment of a tissue region of the brain of a patient comprising:
    an outer catheter having a proximal end, an opening at the proximal end, at least one element and at least one aperture, the outer catheter defining a lumen in communication with respect to the opening and the at least one aperture, the element being adapted to monitor brain activity within the tissue region, to electronically stimulate the tissue region, or to provide information on a precise position of the element when the element is located entirely within the brain and being mounted proximal to a distal end of the outer catheter upon an exterior surface of a distal portion of the outer catheter, the proximal end including an attachment member formed thereat and adapted to be directly attached to the patient's skull after the outer catheter is placed in the tissue region; and
    an inner catheter sized to be received within the lumen and having a passageway and at least one port in communication with respect to the passageway.

2. The catheter assembly of claim 1 further comprising a rigid stylet sized to be received within the lumen for inserting the outer catheter into the patient's brain, the stylet being removed prior to insertion of the inner catheter into the lumen.

3. The catheter assembly of claim 1 wherein the outer catheter has an axis and the aperture is in axial alignment with the lumen.

4. The catheter assembly of claim 1 wherein the outer catheter has a closed distal end and a distal portion at the distal end, the aperture being spaced from the distal end along the distal portion.

5. The catheter assembly of claim 4 wherein the outer catheter has an axis and at least first and second apertures in communication with respect to the lumen, the first and second apertures being spaced axially along the distal portion.

6. The catheter assembly of claim 4 wherein the outer catheter has an axis and at least first and second apertures in communication with respect to the lumen, the first and second apertures being spaced radially about the axis along the distal portion.

7. The catheter assembly of claim 1 wherein the inner catheter has an axis, a distal portion and at least two ports in communication with respect to the passageway, the ports being spaced axially along the distal portion.

8. The catheter assembly of claim 1 wherein the inner catheter has an axis, a distal portion and at least two ports in communication with respect to the passageway, the ports being spaced radially about the axis and spaced axially along the distal portion.

9. The catheter assembly of claim 1 wherein the element is a contact that monitors brain activity.

10. The catheter assembly of claim 9 wherein the contact monitors electrical activity within the brain.

11. The catheter assembly of claim 9 wherein the contact is a micro-contact.

12. The catheter assembly of claim 1 wherein the element is a location marker to identify the position of the outer catheter when inserted within the brain.

13. The catheter assembly of claim 1 wherein the element is at least one sensor.

14. The catheter assembly of claim 13 wherein the sensor senses temperature changes within the patient's brain.

15. The catheter assembly of claim 1 wherein the outer catheter has a distal portion and the at least one element is a plurality of elements spaced axially and radially along the distal portion.

16. The catheter assembly of claim 1 wherein the outer catheter has at least one proximal-contact at the proximal end, the proximal-contact being conductively connected with at least one element through a lead.

17. The catheter assembly of claim 16 wherein the lead is electrical wiring.

18. The catheter assembly of claim 16 wherein the lead is a fiber-optic bundle.

19. The catheter assembly of claim 1 wherein the element is a contact that provides electrical stimulation to a tissue region within the patient's brain.

20. The catheter assembly of claim 1 wherein the attachment member is an externally-threaded proximal portion such that the outer catheter is configured to be screwed into the skull.

21. The catheter assembly of claim 1 wherein the inner catheter fittingly engages the outer catheter such that the inner catheter is firmly secured to the outer catheter.

22. The catheter assembly of claim 21 wherein the inner catheter has an externally-threaded proximal portion threadably received by the outer catheter.

23. The catheter assembly of claim 22 wherein the inner catheter further includes a proximal head having a proximal fitting projecting outward and a flexible conduit removably attached to the proximal fitting and extending between the proximal fitting and a tapered inlet, the inlet being in communication with the passageway such that a pumping instrument can be connected to the inlet to transfer a fluid through the passageway.

24. The catheter assembly of claim 1 wherein the port includes a dialysis membrane adapted to receive cerebral spinal fluid.

* * * * *